(12) United States Patent
Soper et al.

(10) Patent No.: US 10,429,376 B2
(45) Date of Patent: Oct. 1, 2019

(54) MICROFLUIDIC ISOLATION OF TUMOR CELLS OR OTHER RARE CELLS FROM WHOLE BLOOD OR OTHER LIQUIDS

(75) Inventors: Steven A. Soper, Baton Rouge, LA (US); Michael C. Murphy, Baton Rouge, LA (US); June Feng, Shreveport, LA (US); Robin L. McCarley, Prairieville, LA (US); André A. Adams, Burke, VA (US)

(73) Assignee: BOARD OF SUPERVISORS OF LOUISIANA STATE UNIVERSITY AND AGRICULTURAL AND MECHANICAL COLLEGE, Baton Rouge, LA (US)

(*) Notice: Subject to any disclaimer, the term of this patent is extended or adjusted under 35 U.S.C. 154(b) by 1157 days.

(21) Appl. No.: 12/992,225

(22) PCT Filed: May 13, 2009

(86) PCT No.: PCT/US2009/043697
§ 371 (c)(1),
(2), (4) Date: Dec. 7, 2011

(87) PCT Pub. No.: WO2009/140326
PCT Pub. Date: Nov. 19, 2009

(65) Prior Publication Data
US 2012/0100521 A1  Apr. 26, 2012

Related U.S. Application Data

(60) Provisional application No. 61/053,727, filed on May 16, 2008.

(51) Int. Cl.
*B01L 3/00* (2006.01)
*G01N 33/49* (2006.01)
(Continued)

(52) U.S. Cl.
CPC ............ *G01N 33/49* (2013.01); *B01L 3/5027* (2013.01); *G01N 15/1459* (2013.01);
(Continued)

(58) Field of Classification Search
CPC ....... B01L 3/502753; B01L 2200/0668; B01L 2200/10; B01L 2300/0816;
(Continued)

(56) References Cited

U.S. PATENT DOCUMENTS

| 5,637,469 A | 6/1997 | Wilding et al. |
| 5,842,787 A * | 12/1998 | Kopf-Sill ............. B01J 19/0093 366/340 |

(Continued)

FOREIGN PATENT DOCUMENTS

| EP | 1337134 | 8/2004 |
| WO | WO/2006/108087 | 10/2006 |

(Continued)

OTHER PUBLICATIONS

Adams, A. et al., "Highly efficient circulating tumor cell isolation from whole blood and label-free enumeration using polymer-based microfluidics with an integrated conductivity sensor," *J. Am. Chem. Soc.*, vol. 130, pp. 8633-8641 (2008).

(Continued)

*Primary Examiner* — Dean Kwak

(57) ABSTRACT

Microdevices are disclosed to efficiently, accurately, and rapidly isolate and enumerate rare cells, such as circulating tumor cells, from liquids such as whole blood. The system employs multiple parallel meandering channels having a width on the order of 1-2 cell diameters. The microdevices can be produced at low-cost, may readily be automated, and in many instances may be used without pre-processing of the sample. They may be used to isolate and enumerate rare cells, including for example the detection and diagnosis of (Continued)

cancers, cancer staging, or evaluating the effectiveness of a therapeutic intervention, or detecting pathogenic bacteria. The device may optionally be used to nondestructively capture and later to release target cells.

2 Claims, 10 Drawing Sheets

Specification includes a Sequence Listing.

(51) Int. Cl.
*G01N 15/14* (2006.01)
*G01N 15/10* (2006.01)

(52) U.S. Cl.
CPC ..... *G01N 15/1484* (2013.01); *G01N 33/4915* (2013.01); *B01L 2300/0645* (2013.01); *B01L 2300/0816* (2013.01); *B01L 2300/0864* (2013.01); *B01L 2300/0883* (2013.01); *G01N 2015/1006* (2013.01)

(58) Field of Classification Search
CPC ..... B01L 2300/0819; B01L 2300/0858; B01L 2400/0421; B01L 2400/0487; B01L 3/5027; B01L 3/502707; B01L 7/52; B82Y 30/00; B82Y 5/00; B01J 19/0093
USPC .................................................. 422/500–504
See application file for complete search history.

(56) References Cited

U.S. PATENT DOCUMENTS

| | | | | |
|---|---|---|---|---|
| 7,736,050 | B2* | 6/2010 | Park | B01F 5/0475 366/162.1 |
| 8,007,725 | B2* | 8/2011 | Guzman | G01N 27/44743 204/450 |
| 2002/0019059 | A1* | 2/2002 | Chow et al. | 436/514 |
| 2003/0091476 | A1 | 5/2003 | Zhou et al. | 422/102 |
| 2003/0113925 | A1* | 6/2003 | Gordon | G01N 15/1475 506/3 |
| 2006/0113727 | A1 | 6/2006 | Harris et al. | 273/243 |
| 2006/0134599 | A1 | 6/2006 | Toner et al. | |
| 2006/0207877 | A1 | 9/2006 | Schmidt et al. | 204/400 |
| 2007/0026413 | A1 | 2/2007 | Toner | 435/287.2 |
| 2007/0026416 | A1* | 2/2007 | Fuchs | B01L 3/502746 435/6.16 |
| 2007/0092876 | A1* | 4/2007 | Xu | C12N 15/1003 435/6.12 |
| 2007/0172903 | A1 | 7/2007 | Toner | 435/325 |
| 2007/0172954 | A1* | 7/2007 | Ismagilov | B01F 5/0646 436/53 |
| 2007/0191703 | A1 | 8/2007 | Graf | 600/410 |
| 2007/0264675 | A1 | 11/2007 | Toner | 435/325 |
| 2008/0014589 | A1* | 1/2008 | Link | B01F 3/0807 435/287.2 |
| 2008/0124721 | A1 | 5/2008 | Fuchs et al. | 435/6 |
| 2008/0318324 | A1* | 12/2008 | Chiu | B01D 63/00 436/64 |
| 2009/0014360 | A1* | 1/2009 | Toner | B01D 21/0087 209/208 |
| 2009/0155877 | A1* | 6/2009 | Iliescu | B01L 3/502707 435/173.7 |
| 2010/0112723 | A1* | 5/2010 | Battrell et al. | 436/501 |
| 2010/0203521 | A1* | 8/2010 | Klapperich | B01L 3/502707 435/6.13 |
| 2012/0149872 | A1 | 6/2012 | Belgrader | |

FOREIGN PATENT DOCUMENTS

| | | |
|---|---|---|
| WO | WO/2006/113727 | 10/2006 |
| WO | WO 2006113727 A2 * | 10/2006 |
| WO | 2006119806 A2 | 11/2006 |
| WO | WO/2008/130977 | 10/2008 |

OTHER PUBLICATIONS

Dharmasiri, U. et al., "Highly efficient capture and enumeration of low abundance prostate cancer cells using prostate-specific membrane antigen aptamers immobilized to a polymeric microfluidic device," *Electrophoresis*, vol. 30, No. 18, pp. 3289-3300 (2009).

Lupold, S. et al., "Identification and Characterization of Nuclease-stabilized RNA Molecules That Bind Human Prostate Cancer Cells via the Prostate-specific Membrane Antigen," *Cancer Res.*, vol. 62, pp. 4029-4033 (2002).

Nagrath, S. et al., "Isolation of rare circulating tumour cells in cancer patients by microchip technology," *Nature*, vol. 450, No. 7173, pp. 1168-1169 or 1235-1239 (2007).

Phillips, J. et al., "Enrichment of Cancer Cells Using Aptamers Immobilized on a Microfluidic Channel," *Anal. Chem.*, vol. 81, pp. 1033-1039 (2009).

Sethu, P. et al., "Continuous flow microfluidic device for rapid erythrocyte lysis," *Anal. Chem.*, vol. 76, pp. 6247-6253 (2004).

Toner, M. et al., "Blood-on-a-Chip," Annu. Rev. Biomed. Eng., vol. 7, pp. 77-103 (2005).

Adams, A. et al., "Low abundant biomarker screening in poly(methylmethacrylate) high aspect ratio microstructures using immunoaffinity-based molecular recognition," Special Publication: Royal Society of Chemistry—Minaturized Total Analysis Systems, vol. 1, pp. 132-134 (2004).

Supplementary European Search Report for EPO Application No. 09747410, dated Oct. 24, 2017, 7 pages.

USPTO, Non-Final Rejection in U.S. Appl. No. 15/935,585 dated Apr. 1, 2019.

Amendment and response to Supplementary European Search Report for EPO Application No. 09747410, dated Aug. 16, 2018, 16 pages.

* cited by examiner

MICROFLUIDIC ISOLATION OF TUMOR CELLS OR OTHER RARE CELLS FROM WHOLE BLOOD OR OTHER LIQUIDS

This is the United States national stage of international application PCT/US2009/043697, international filing date May 13, 2009, which claims the benefit of the May 16, 2008 filing date of U.S. provisional patent application Ser. No. 61/053,727 under 35 U.S.C. § 119(e).

This invention was made with government support under grant 1R33-CA099246-01 awarded by the National Cancer Institute of the National Institutes of Health. The government has certain rights in the invention.

This invention was made with government support under grant EPS-0346411 awarded by the National Science Foundation. The government has certain rights in the invention.

TECHNICAL FIELD

This invention pertains to the isolation of tumor cells or other rare cells from whole blood or other liquids.

BACKGROUND ART

There is an unfilled need for improved techniques to isolate and detect circulating tumor cells and other rare cells.

Most cancer-related mortalities result from metastasis. Cancer cells can be transported from the primary tumor by the circulatory system or bone marrow; some of these circulating cells may have metastatic potential. The ability to identify and count circulating tumor cells (CTCs) would be enormously helpful in the diagnosis and prognosis of many types of cancer. It has proven difficult, however, to reliably detect CTCs due to their extremely low concentration among a high background of "spectator" cells in peripheral blood (e.g., red and white blood cells). It has been reported that the concentration of CTCs in the blood correlates with mean survival time for breast cancer patients. It would be very useful clinically, for example, to be able to accurately count 0-10 CTCs in 1 mL of whole blood in a background of $\sim 10^9$ erythrocytes and $\sim 10^6$ leukocytes.

In sampling rare events from a large population, three important metrics are: (1) throughput, the number of cells identified or the number of sorting steps per unit time; (2) recovery, the fraction of the target cells successfully retrieved from the input sample; and (3) purity, the degree to which the recovered cells are free from "interfering" cells. In addition to these three metrics, the enriched cells must also be counted accurately.

Prior approaches to enriching CTCs in clinical samples have generally produced low recoveries with high purity, or low purity with high recovery. In a handful of cases, both high purity and high recovery have been reported, but only with highly specialized sample processing and handling equipment and techniques. For example, antibody-coated, micron-sized magnetic particles have been used to enrich CTCs with high purity, but only modest recoveries (~70%). Polycarbonate membranes with varying pore sizes (8-14 µm) have been used to filter cells by size from relatively large volumes of blood (9.0-18 mL), with recovery of ~85% of the CTCs, but at low purity due to the retention of large numbers of leukocytes as well.

Another approach has been to use quantitative PCR; or to use reverse-transcription PCR to assay mRNA as a surrogate for CTCs. RT-PCR can detect one CTC in an excess of $10^6$ mononucleated cells. However, RT-PCR assays are prone to high inter-laboratory variability, are notoriously subject to false positives from environmental contamination, and require extensive sample handling and manipulation. Also, PCR techniques will generally destroy the cells being sampled.

Among the difficulties encountered by the existing methods for isolating and counting CTCs are one or more of the following: the need to select rare CTC cells from the mononucleated fraction of whole blood, which typically involves the use of density gradient centrifugation to remove the far more numerous RBCs; the need for flow cytometry apparatus; or the need for fluorescence microscopy. In addition to their cost and complexity, these procedures entail sample handling and transfer steps that can result in cell loss or contamination, which can dramatically affect results, particularly when one is dealing with a very low number of target cells to begin with.

Microfluidic systems can be used to process samples, including clinical samples, so as to minimize sample contamination and loss. However, microfluidic systems have not previously been widely used to process relatively large sample volumes (e.g., ≥1 mL) due to the small dimensions of the devices. For example, to fully process a 1.0 mL sample volume using a 30 µm×30 µm microchannel at a linear velocity of 1.0 mm s$^{-1}$ would require ~309 h (~13 days). One approach has been to prepare a high-surface area immunological capture bed filled with microposts (e.g., ~100 µm diameter×~100 µm tall).

Patent application publication no. US2007/0026413A1 discloses a device with an array of obstacles (e.g., microposts) that relies on the hydrodynamics of flow through gaps between the obstacles, as well as spatial offsets between adjacent rows of the obstacles, and antibodies on the micropost surfaces to preferentially sort cell types by size, shape, chemical composition, or deformability. See also S. Nagrath et al., "Isolation of rare circulating tumour cells in cancer patients by microchip technology," Nature, vol. 450, pp. 1235-1239 (2007); and patent application publication nos. US2007/0264675A1; US2007/0172903A1; US2008/0124721A1 and US2006/0134599A1.

Patent application publication no. US2008/0318324A1 discloses micro-fabricated or nano-fabricated devices for separating, concentrating, and isolating circulating tumor cells or other particles. Fluidic channels having particular cross-sectional shapes or other features could be used for dispersion, distribution, or partition of the fluidic flow, in order to reduce the direct impact of cells against exclusion features. The disclosure describes the use of so-called "effusive filtration"—redirecting, partitioning, dampening, or dispersing fluid flow to reduce physical impact on cells, while still allowing filtration through apertures. In some cases curvature might be included as a feature of the filtration perimeter. The channel surfaces could be treated with anticoagulant compounds, compounds that preferentially bind to circulating tumor cells, or compounds that prevent the sticking of cells.

P. Sethu et al., "Continuous flow microfluidic device for rapid erythrocyte lysis," Anal. Chem., vol. 76, pp. 6247-6253 (2004) discloses a microfluidic device for erythrocyte removal from a blood sample by selectively lysing the erythrocytes. Whole blood was mixed with a lysis buffer, and the mixture was transported through a rectangular-wave microfluidic reaction channel.

M. Toner et al., "Blood-on-a-Chip," Annu. Rev. Biomed. Eng., vol. 7, pp. 77-103 (2005) provides a review of research concerning the use of microdevices for manipulating blood and blood cells at the micro-scale.

Antibodies are not the only molecular recognition elements with high specificity for selected target molecules. Aptamers are another example of recognition elements that can have high specificity. Aptamers are single-stranded nucleic acid oligomers with specific affinity for a molecular target, generally via interactions other than classical Watson-Crick base pairing. In comparison to antibodies, aptamers (generally) have lower molecular weight and higher stability during long-term storage. Automated techniques are known in the art for selecting and synthesizing aptamers having specificity against a desired target, e.g., a membrane protein. Aptamers may readily be immobilized on solid support surfaces such as glass, polymers, or gold.

S. Lupold et al., Cancer Res., vol. 62, pp. 4029-4033 (2002) disclosed RNA aptamers directed against PSMA, and the use of those aptamers to target lymph node metastasis prostate cancer (LNCaP) cells.

J. Phillips et al., Anal. Chem., vol. 81, pp. 1033-1039 (2009) disclosed the use of aptamers on PDMS microchannel walls for the selection of leukemia cells seeded (~1×10$^6$ cells/mL) in an aqueous buffer that was also loaded with non-cancerous cells.

A. Adams et al., "Low abundant biomarker screening in poly(methylmethacrylate) high aspect ratio microstructures using immunoaffinity-based molecular recognition," Special Publication: Royal Society of Chemistry—Miniaturized Total Analysis Systems, vol. 1, pp. 132-134 (2004) disclosed a PMMA high aspect ratio, antibody-decorated, microfluidic device to pre-concentrate low abundant cancer cells from suspensions of simulated blood. An optimum flow rate for this device was found to be 2 mm/s. Antibodies were attached to a carboxylated polymer surface, generated by exposure to UV radiation. The device had 17 straight channels "with extreme rectangular character i.e. narrow (30-50 µm) and tall (250 µm)" to maximize collisions between cells and channel walls. A capture efficiency of 1% was reported for a 50 µm channel, and 100% for a 20 µm channel.

DISCLOSURE OF THE INVENTION

We have discovered a system to efficiently, accurately, and rapidly isolate and enumerate rare cells, such as circulating tumor cells, from liquids such as whole blood. It is now possible to exhaustively and rapidly interrogate large volumes (e.g., 1.0 mL or more) of unprocessed whole blood for rare cells, such as CTCs. Rare cells have successfully been isolated and detected in prototype experiments when the background cells outnumbered target cells by eight orders of magnitude; and even higher levels of sensitivity should be possible.

In a prototype embodiment of the novel high-throughput microsampling unit (HTMSU), we have designed and successfully tested exceedingly efficient, high-aspect ratio capture beds decorated with monoclonal antibodies (mABs) or aptamers specific for CTC membrane proteins. The HTMSU has parallel, meandering (preferably sinusoidal or quasi-sinusoidal) fluid channels with a width on the order of 1-2 cell diameters. A preferred embodiment employs a label-free, highly specific conductivity sensor for the non-destructive detection of single cells. Tumor cells often have higher electrical conductivities than normal cells, for example, due to over-expression of charged membrane proteins or glycoproteins, such as those with sialic acid molecules. This difference lends itself to detection by conductivity measurements. A preferred method for attaching capture elements is the photoresist-free micropatterning technique disclosed in United States patent application publication no. US2007/0191703A1. Using this technique the capture elements can be selectively attached to just the channel walls, without also being attached to other portions of the device. Selectively attaching the capture elements to only the channel walls is preferred, and helps promote high recovery of the target cells. By contrast, attaching capture elements outside the channels could cause cells to anchor to spots in "unswept void volumes" that might not later be released; while not preferred in general, in some specific applications it could be useful also to attach capture elements to other surfaces within the device, surfaces outside the channels themselves. The hydrodynamics are generally better-tuned within the capture channels than in the other areas of the device, and it is therefore preferred to capture the cells only within the channels. We note that the side walls of the channels can be exposed with a conventional mask and UV irradiation, because the light is typically not fully collinear. There are divergent light rays that hit the side walls. Also, there will be scattering that causes the side walls to be exposed to the UV radiation.

Devices in accordance with the present invention can be produced at low-cost using micro-replication and fabrication technologies that are otherwise known in the art. The devices may readily be automated, and in many instances may be used without requiring any pre-processing of the sample. The novel system may be used in many situations where it is desirable to isolate and enumerate rare cells, including for example the detection and diagnosis of cancers, cancer staging, evaluating the effectiveness of a therapeutic intervention, or detecting pathogenic bacteria (e.g., in food or in environmental samples).

The HTMSU system is flexible, and may accommodate a wide variety of molecular recognition elements (antibodies, aptamers, etc.) to target particular types of rare cells. As one example, the channel walls could be decorated with monoclonal antibodies directed against E. coli O157:H7 to detect that pathogenic bacterial strain at extremely low concentrations.

Preferred embodiments of the novel system employ one or more of the following features or characteristics: "walled-in" channels rather than posts are used for fluid flow and cell capture; posts, although not preferred, may optionally also be present, but not to the exclusion of "walled-in" channels; multiple parallel channels are preferred to enhance throughput; sinusoidal, quasi-sinusoidal, or other meandering channel shape is used to enhance contact between cells in the fluid and the channel walls; a very high capture efficiency is obtained; the channels have a high aspect ratio (3:1 or more); the channel width should be on the order of 1-2 cell diameters; there is a uniform or near-uniform pressure drop across the multiple channels; the device material chosen to inhibit non-specific binding, PMMA is often useful for this purpose; highly-specific capture elements are used, e.g., monoclonal antibodies or aptamers; the device is readily scalable by changing the channel depth, the number of channels, or both; and the device may be used to nondestructively capture and later to release target cells.

Recovery efficiencies of rare cells can be very high: 80%+, 85%+, 90%+, 95%+, 97%+. These rates are superior to any that have previously been reported with other devices or systems. Additionally, the rate of false positives can be very low, e.g., less than 1 per 10 mL of sample. A low rate of false positives can be achieved by incorporating several independent modes of specificity into the device and its operation; preferred embodiments employ molecular recognition (e.g., monoclonal antibody), shear force to remove non-target cells that may be non-selectively adhering to the surface, and the use of a detector that is selective for cells having the same size as the target cells. The invention may be used to recover rare cells from a variety of liquids, including whole blood, water, urine, saliva, CSF, and others.

MODES FOR CARRYING OUT THE INVENTION

Examples 1-21

Fabrication of Prototype HTMSU, and Isolation and Detection of Low Abundance MCF-7 Breast Cancer Cells in Whole Blood Materials and Methods Example 1

HTMSU Fabrication

Figure 1:
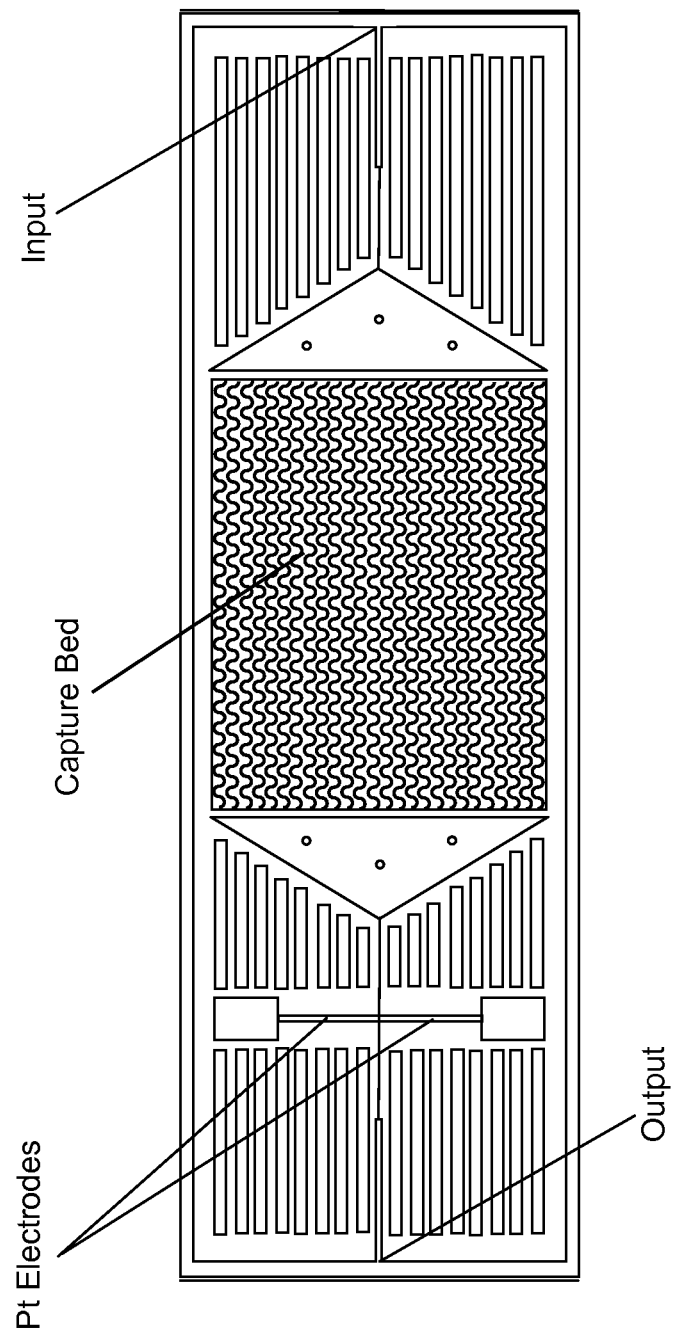
FIG. 1 depicts schematically a prototype HTMSU in accordance with the present invention.

FIG. 1 depicts schematically a prototype HTMSU in accordance with the present invention. The prototype HTMSU has been successfully fabricated and tested. The prototype device contained 51 high-aspect-ratio, sinusoidal, parallel channels that shared a common input port and a common output port. Devices were replicated from a master mold using hot embossing techniques that are otherwise known in the art. See A. Adams et al., "Highly efficient circulating tumor cell isolation from whole blood and label-free enumeration using polymer-based microfluidics with an integrated conductivity sensor," *J. Am. Chem. Soc.*, vol. 130, pp. 8633-8641 (2008), and the supporting material that is available at pubs.acs.org for additional details concerning the fabrication of the master mold and the micro-replication procedures, the complete disclosures of which are incorporated by reference. The substrate used in the prototype HTMSU was poly(methyl methacrylate) (PMMA), which was chosen for its high fidelity in replicating high-aspect ratio microstructures, its minimal non-specific adsorption of whole blood components, and the ability to functionalize the surface of PMMA with different moieties through UV irradiation.

Example 2

Antibody Immobilization

Antibodies were immobilized in a two-step process. First, the UV-surface-modified HTMSU device was loaded with a solution containing 4.0 mg/mL of 1-ethyl-3-[3-dimethylaminopropyl]carbodiimide hydrochloride (EDC), 6.0 mg/mL of N-hydroxysuccinimide (NHS) in 150 mM 2-(4-morpholino)-ethane sulfonic acid at pH=6 (MES, Fisher Biotech, Fair Lawn, N.J.); and buffered saline (Sigma-Aldrich, St. Louis, Mo.) for 1.0 hr to form a succinimidyl ester intermediate. The EDC/NHS solution within the device was then hydrodynamically replaced with a 1.0 mg/mL solution of monoclonal anti-EpCAM antibody (R&D Systems Inc., Minneapolis, Minn.) in 150 mM PBS at pH=7.4 (Sigma-Aldrich, St Louis, Mo.), which was allowed to react for 4 hours. The device was then rinsed with a solution of PBS (pH=7.4) to remove any unbound anti-EpCAM antibodies. For additional details concerning these procedures, see the Adams et al. Supporting Information (2008), hereby incorporated by reference.

Example 3

Apparatus

A PHD2000 syringe pump (Harvard Apparatus, Holliston, Mass.) was used to hydrodynamically process samples in the prototype HTMSU. A luer lock syringe (Hamilton, Reno, Nev.) was fitted with a luer-to-capillary adapter (InnovaQuartz, Phoenix, Ariz.) to connect the HTMSU and the pump. The flow rate of the syringe pump was programmable. The linear velocities were calculated, based on the ratio of the cross-sectional area of the HTMSU capture channels to the programmed volumetric flow rate. The flow rates were confirmed by tracking suspended cells over a fixed 80 μm region via optical microscopy.

The prototype HTMSU was fixed to a programmable, motorized stage of an Axiovert 200M (Carl Zeiss, Thornwood, N.Y.) microscope, which could monitor cells in the HTMSU by fluorescence or bright field imaging. Videos of cell transport were captured at 30 frames per second using a monochrome CCD (JAI CV252, San Jose, Calif.). For fluorescence observation of MCF-7 cells, dyes were excited with a Xe arc lamp and dye-specific filter sets (Carl Zeiss, Thornwood, N.Y.). Each filter cube contained a dichroic mirror, emission filter, and excitation filter.

Example 4

Integrated Conductivity Sensor

The conductivity electrodes were Pt wires (~75 μm) in guide channels embossed into the fluidic network and positioned orthogonal to the fluid output channel. The Pt wire was inserted into the guide channels prior to thermal bonding of the cover plate to the substrate. Once the wire was positioned, the substrate/wire assembly was placed between glass plates and clamped together and heated to slightly above the glass transition temperature of PMMA, to embed the wire into the guide channels. The wire spanned the entire depth of the output channel. The wire was then cut to form an electrode pair, using a high precision micromilling machine (KERN MMP 2522, KERN Micro- and Feinwerktechnik GmbH & Co.; Eschenlohe Germany) with a 50 µm bit. Following machining of the Pt wire and UV activation of the channel polymer surfaces, the cover plate was aligned with the embossed substrate via alignment marks, and the assembly was clamped between two glass plates and heated to bond the components to one another.

For further details concerning the preferred conductivity sensor, see D. Patterson, "Conductivity Counter," U.S. patent application Ser. No. 12/388,904, filed Feb. 19, 2009; and the Adams et al. supporting material (2008); the complete disclosures of both of which are incorporated by reference.

Conductivity was measured in TRIS-glycine buffer containing 0.25% (w/w) trypsin, 0.18 mM TRIS, 47 mM glycine, and 0.05% (v/v) Tween-20, sometimes referred to as the "CTC-releasing buffer." The CTC-releasing buffer had a relatively low conductivity (~50 µS/cm, pH 7.2). The trypsin in the CTC-releasing buffer acts to remove bound cells (CTCs) from the capture channel surface.

Example 5

Cell Suspensions

Citrated whole rabbit blood was purchased from Colorado Serum Company (Denver, Colo.). (The blood contained 10% (w/w) sodium citrate to inhibit coagulation.) The MCF-7 cells (a breast cancer cell line), growth medium, phosphate buffered saline, trypsin, and fetal bovine serum were purchased from the American Type Culture Collection (Manassas, Va.). Adherent MCF-7 cells were cultured to 80% confluence in Dulbecco's modified Eagle's Medium supplemented with high glucose, and containing 1.5 g $L^{-1}$ sodium bicarbonate ($NaHCO_3$), 15 mM HEPES buffer, and 10% fetal bovine serum (FBS).

Some of the MCF-7 cells were stained for fluorescence visualization experiments with PKH67, a fluorescein derivative that contains a lipophilic membrane linker (Sigma-Aldrich, St. Louis, Mo.). The manufacturer's suggested protocol for cell staining was modified by doubling the dye concentration, so that the fluorescent labels were more evenly distributed over the cell membranes. The cell counts in whole blood seeding experiments were determined by counting three aliquots of cells with a hemocytometer. The cell count accuracy was ±10%.

Results and Discussion (MCF-7 Cell Experiments)

Model CTC System.

We used the MCF-7 cell line as a model for CTC selection and enumeration with the prototype HTMSU. MCF-7 is a breast cancer cell line that over-expresses the membrane-bound molecule epithelial cell adhesion molecule (EpCAM). MCF-7 cells are ~15-30 µm in diameter (mean=24 µm). They have been closely associated with micro-metastatic breast cancer. MCF-7 membranes have an average of ~$5.1\times10^5$ EpCAM molecules per cell. Monoclonal antibodies for EpCAM are commercially available.

We found several experimental and device parameters that affected the performance of the HTMSU. We have taken preliminary steps towards optimizing these parameters to enhance performance of the HTMSU. Among these parameters are the following: (1) Throughput—linear flow velocity, pressure drop, processing time; (2) recovery—capture channel geometry (shape and width), cell flow dynamics; (3) purity—surface design to minimize non-specific adsorption and to provide high selectivity for target cells.

Example 6

Pressure Drop

A primary goal for the prototype HTMSU was to process whole blood directly in a reasonable time. We designed high-aspect ratio capture channels to enhance throughput. (Aspect ratio=channel height/channel width.) If the channel width and height were both on the order of the cell dimensions (aspect ratio≈1), then the capture of even a single cell within a channel would cause a large pressure drop, and could possibly damage the captured cell. Other potential sources of obstruction also become more likely when both the width and the height are small. For the prototype device we chose a capture channel with an aspect ratio of 4.3:35 µm wide by 150 µm deep. These dimensions may readily be reproduced by hot embossing techniques otherwise known in the art. Assuming a blood viscosity of 4.8 cP (hematocrit=0.4), we calculated that the pressure drop for a channel 35 µm×35 µm (L=3.5 cm) would be ~$7.4\times10^3$ Pa, while the pressure drop for a 35 µm×150 µm channel would be ~$2.9\times10^3$ Pa, a reduction of more than 60%.

Examples 7-10

Flow Dynamics

When a capillary has dimensions more than ~15% larger than the dimensions of the cells being transported, the cells tend to migrate toward the central axis of the tube, and to leave a cell-free layer adjacent to the capillary wall, typically ~4 µm thick. Because the capture elements (e.g., antibodies) are tethered to the channel wall, this "focusing" away from the wall tends to reduce the number of encounters between target cells (e.g., CTCs) and the recognition elements. To investigate this phenomenon quantitatively, we stained CTCs with a membrane-specific fluorescein derivative, and imaged them as they were transported through unmodified (no mAB), 35 µm-wide microchannels with either a straight or a sinusoidal configuration. The results of these experiments are shown in FIGS. 2A-D FIGS. 2A-D are histograms depicting the observed radial position of CTCs in microchannels at linear velocities (U) of 1.0 mm/s (FIGS. 2A and C) and 10 mm/s (FIGS. 2B and D); in straight (FIGS. 2A and B) and sinusoidal (FIGS. 2C and D) channels. The central lines represent the microchannel's central axis. The cells were stained with a fluorescein lipophilic membrane dye, PKH67, and were imaged by fluorescence microscopy.

Figure 2A:
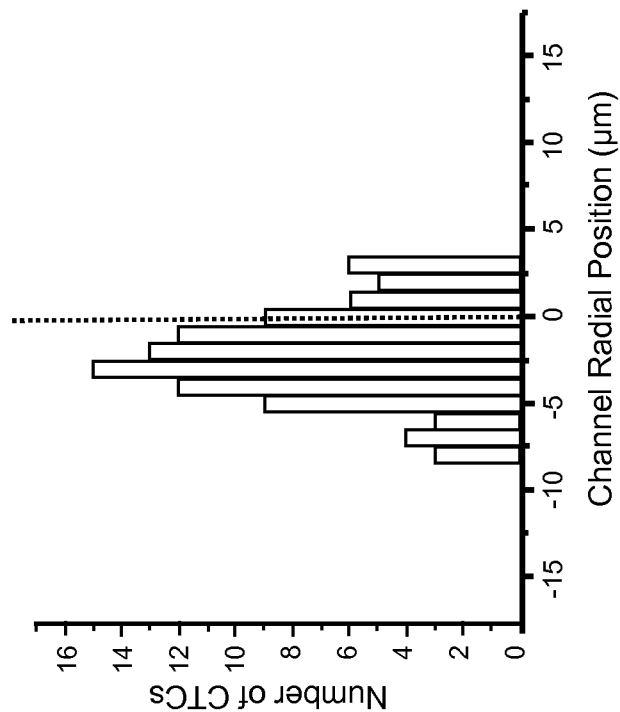
FIGS. 2A-D are histograms depicting the observed radial position of CTCs in different shaped microchannels at different velocities.
Figure 2B:
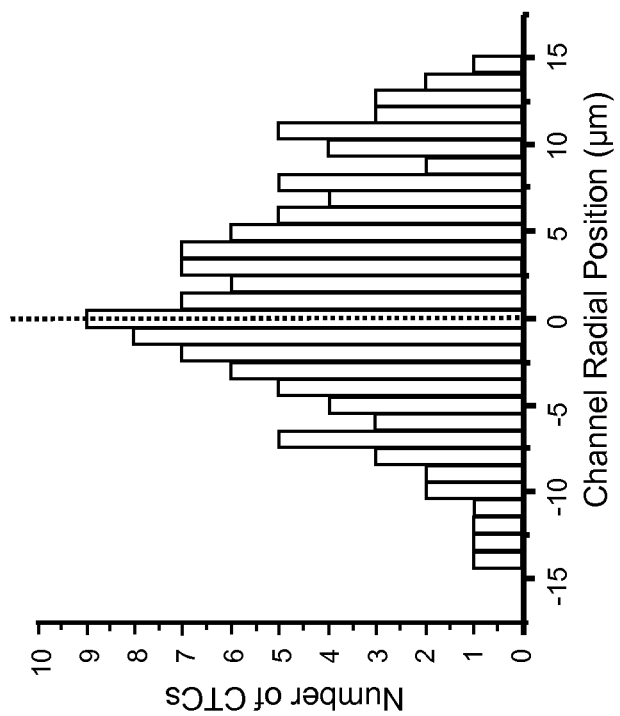
Figure 2C:
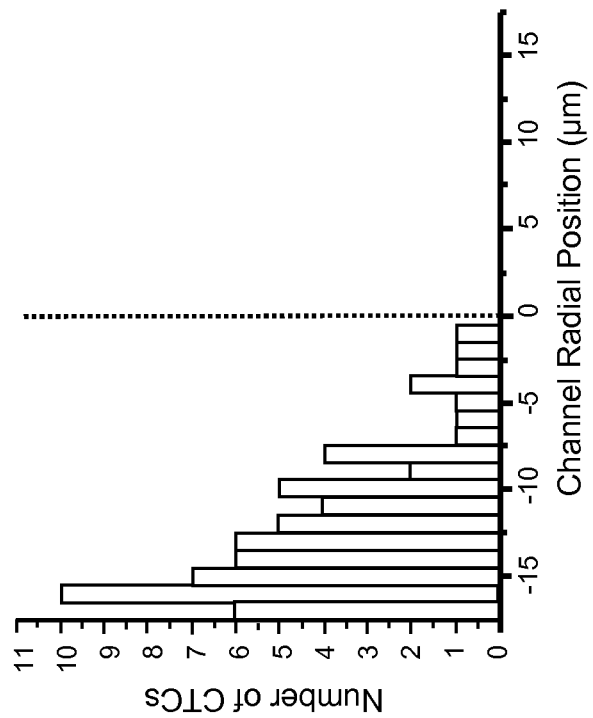
Figure 2D:
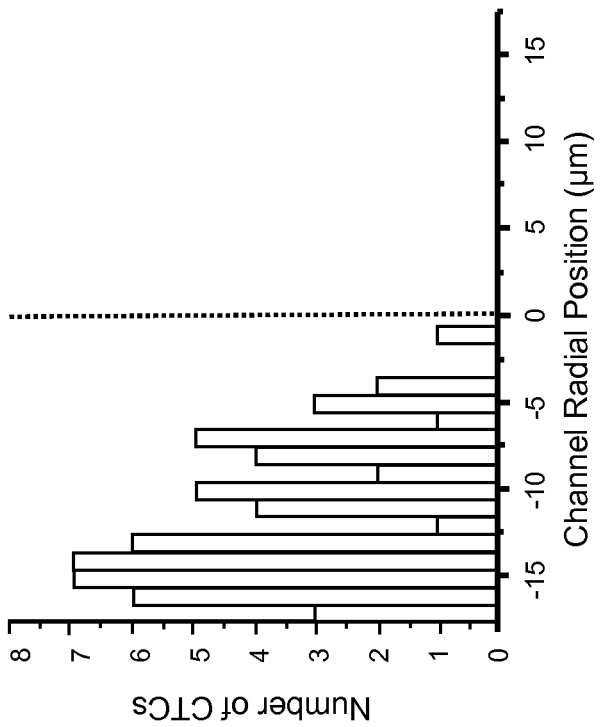

The straight channels (FIGS. 2A and B) displayed a cell-free zone, similar to what has been observed in straight capillaries. The thickness of this cell-free zone increased with increased velocity U. The observed flow dynamics were quite different in the sinusoidally-shaped channels (FIGS. 2C and D). First, no marginal zone appeared along the edge of the microchannel wall, and second, the radial distribution of cells seemed to be largely independent of changes in U. Thus more efficient capture of cells results when sinusoidal (or quasi-sinusoidal, or other meandering) channels are used—even when relatively high linear velocities are used to process large input volumes over relatively short times. Without wishing to be bound by this hypothesis, we believe that the cells migrate to the outside of the curved channel primarily due to two factors: (1) a cross-stream velocity component due to the reversal of the direction of curvature, which promotes re-circulation and mixing; and (2) centrifugal force acting on the cells, which tends to "push" cells toward the outer walls.

We also calculated the Reynolds number and the Dean number for the 35 µm, curved channels. The Dean number is a dimensionless quantity that accounts for both the radius of curvature and the hydraulic diameter of a curved channel. For the sinusoidal channels used in our prototype devices, the Dean number was calculated to be ~1.1 at a translational velocity of 10 mm s$^{-1}$, well below the threshold value of ~36 at which the flow becomes unstable.

Figure 7:
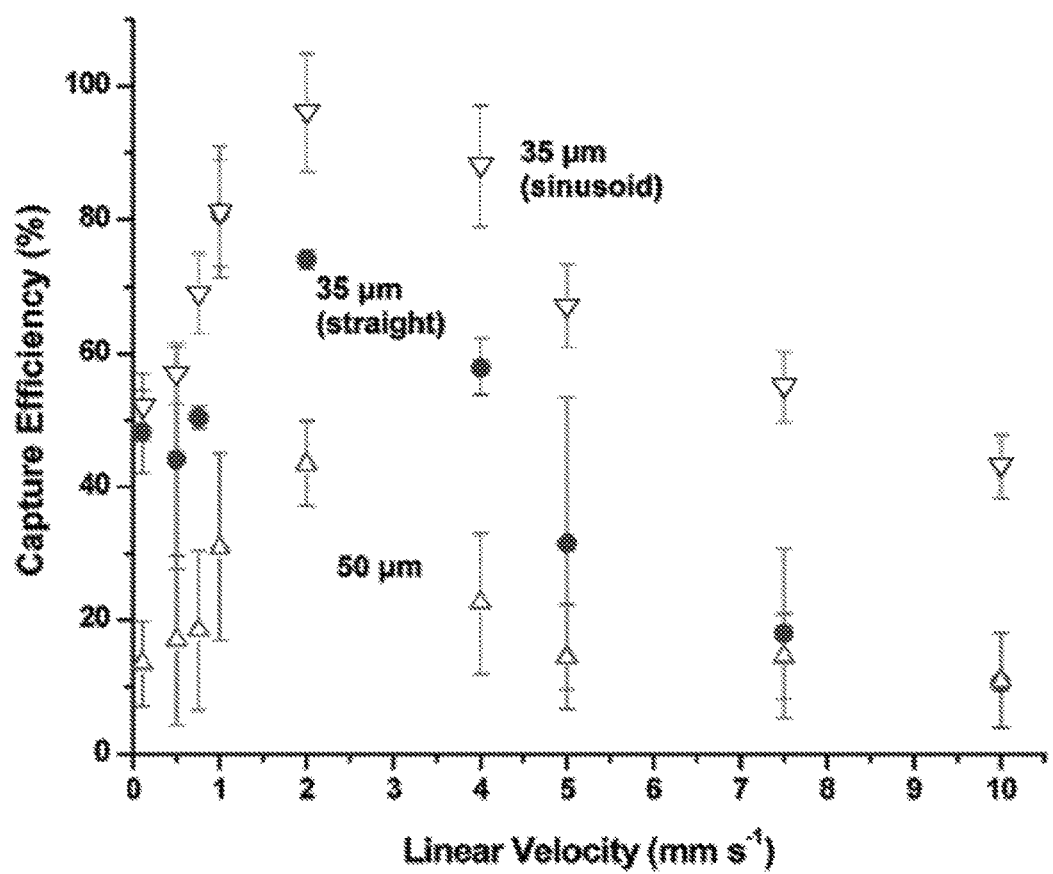
FIG. 7 depicts data showing the capture efficiency of CTCs in spiked whole blood samples as a function of the cells' translational velocity using 35 (down triangles, sinusoid; circles, straight), and 50 μm (up triangles) wide microchannels. The microfluidic device consisted of a single channel with the appropriate width and a depth of 150 μm.

We examined the effects of varying the dimensions and shape of the capture channels, and the linear flow velocity. We measured CTC capture efficiency in straight channels 20, 35, and 50 µm wide, and in a 35 µm-wide sinusoidal channel, at various flow rates. The results of these studies are depicted in FIG. 7 as plots of CTC capture efficiency (5) versus linear velocity, U (mm s$^{-1}$).

The 20 µm-wide, straight channel trapped essentially 100% of the target cells before entering the channel, at all flow rates investigated. Observation by fluorescence microscopy revealed that most cells did not even enter the capture channel, because the CTCs were typically wider than the 20 µm channel. For those cells that did enter the channels, the cell membranes were in constant proximity to the antibody-coated channel walls, and were typically captured within the first 1-2 mm of the 3.5 cm-long channel. The 20 µm device consistently failed from microchannel blockage in these tests, and we consider it to be too narrow to be used for many cell types (although such a width or even narrower might be practical for capturing smaller cells, such as bacteria). Furthermore, at higher linear flow velocities blockages can lead to unacceptable head pressures. For these reasons it is preferred to use a channel width that is at least as large as the diameter of the average target cell.

We also observed that for all channel widths above 20 µm, in both linear and sinusoidal channels, the cell capture efficiency reached a maximum at a linear flow velocity ~2 mm s$^{-1}$. Capture efficiency declined at both faster and slower flow rates. Capture efficiency was higher for narrower channel widths, provided that the channel was not so narrow that it was readily susceptible to blockage. The highest capture efficiency was obtained with the sinusoidal-shaped, 35 µm-wide channel (~97%). This optimal flow velocity will vary, depending on the particular type of cell targeted, and the particular capture element used.

A device with a single 35×150 µm channel, operated at a linear flow rate of ~2 mm s$^{-1}$, would process 1 mL of fluid in ~9.5×10$^5$ s (~26 h). Increasing the linear flow rate would decrease capture efficiency, so we instead designed a prototype device with multiple capture channels (all of similar dimensions), having a single, common input and a single, common output. The prototype device had 51 capture channels, reducing the processing time for 1 mL of fluid to ~1900 s (~31 min). Using a common output for all the capture channels allowed for simple collection and pooling of the selected cells. The 51-channel prototype device is depicted in FIG. 1. If the channel depth were increased to 250 µm (an aspect ratio of 7.14 for a 35 µm-wide channel), and if the number of parallel channels were doubled, then the sampling time for this same volume input could be reduced to ~2.7 min. Also, larger sample volumes (e.g., 10 mL or more) could be processed in a reasonable time.

Examples 15-16

Shear Effects on Captured Cells

We also evaluated shear forces on captured cells, to determine whether flow-induced shear could either detach the cells from the walls or damage the cells. Using a simple model of the forces involved, we calculated that the linear flow velocity required to detach the EpCAM-expressing cells from a PMMA wall decorated with anti-EpCAM antibodies would be on the order of $10^2$ to $10^4$ cm s$^{-1}$, depending on the degree to which the captured cells were flattened and elongated on the antibody-decorated surface. This range of velocities is substantially greater than the flow rates used in our experiments, implying that shear forces should not be expected to present difficulties. We observed several captured cells continuously during tests employing linear velocities up to 10.0 cm s$^{-1}$; neither cell damage nor disruption of cell-wall adhesion was seen.

Example 17

Detaching and Counting Intact Cells

After cells have been captured, it will usually be desirable to selectively release the captured cells at a later time without damaging them, for example to count or otherwise characterize them. There are strong adhesion forces in a typical antigen-antibody system, so an enzymatic or other selective releasing mechanism should be used. For example, we have successfully used the proteolytic enzyme trypsin to release captured cells undamaged. Proteolytic digestion and release of the captured cells typically required less than 10 minutes.

Examples 18-20

Conductivity Sensor for Cell Enumeration

Two integrated Pt electrodes, 50 µm apart, were used in a conductivity sensor to count cells. The characteristic parameter K (the ratio of the electrode gap to the electrode area) was chosen as ~0.01 µm$^{-1}$ to detect larger, target CTCs preferentially over smaller leukocytes or erythrocytes that might still be present in small numbers as the result of non-specific adsorption.

Figures 3A, 3B:
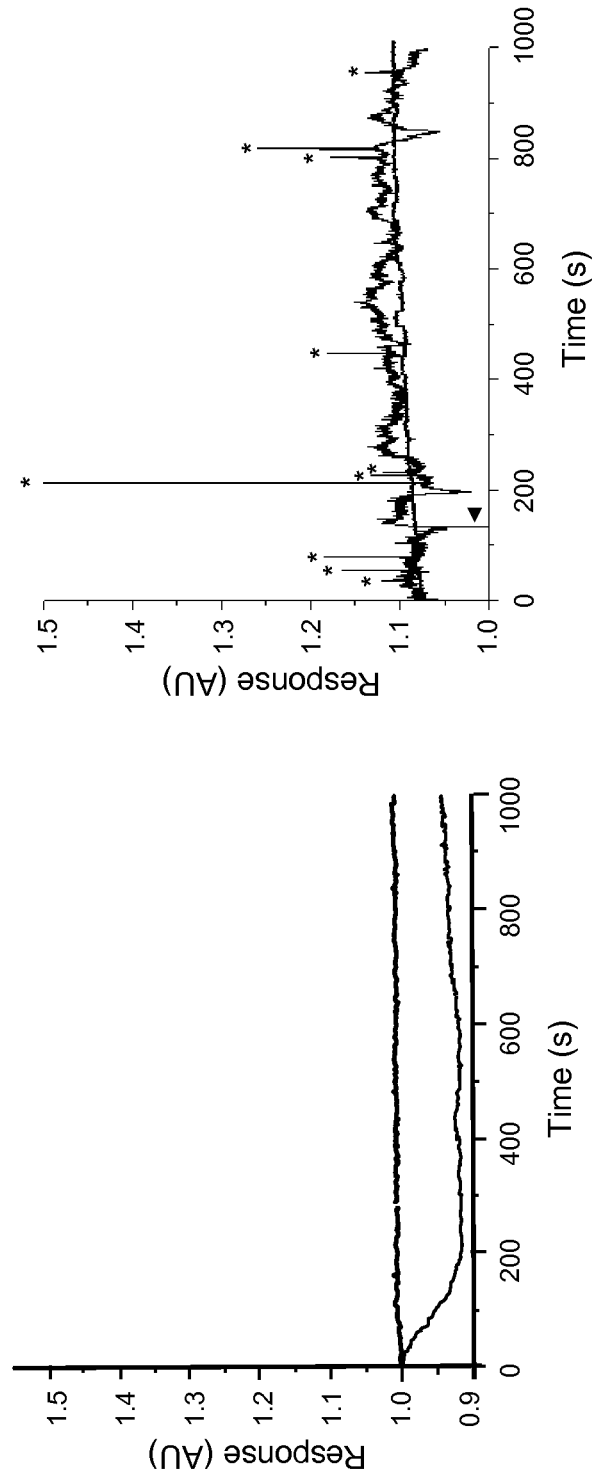
FIGS. 3A-C depict the results of various conductance measurements with the novel system, using MCF-7 breast cancer cells and whole blood.
Figure 3C:
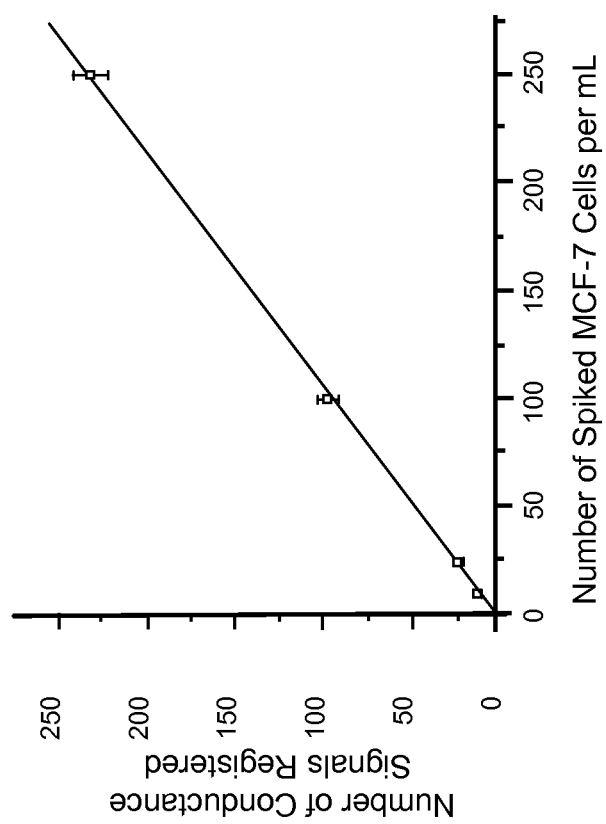

The capture channels of the prototype HTMSU were tapered from 150 µm to a depth of ~80 µm as they approached the conductivity sensor, in order to match the Pt electrode diameter and to have a sampling efficiency near 100%. FIGS. 3A-C depict the results of various conductance measurements. FIGS. 3A and B depict conductance responses, in arbitrary units (AU). FIG. 3A depicts the response of the electrodes to test samples spiked with leukocytes (lower curve) or erythrocytes (upper curve). In both cases the cell density was 150 cells/µL, in TRIS-Glycine buffer, transported through the integrated conductivity sensor at a flow rate of 0.05 µL/min. We observed that the electrodes were essentially insensitive to both leukocytes and erythrocytes. Briefly: the conductivity sensor is sensitive to changes in the local bulk solution conductance. When a single cell traverses the electrode pair, a change in the measured local bulk conductivity can result. RBCs produced no appreciable signal, simply as a result of their small size. The conductance of WBCs is similar to that of the carrier buffer, resulting in no apparent signal. However, the conductance of CTCs will generally differ from that of the buffer, allowing them to be selectively detected.

The chemical composition of CTCs makes their electrical properties distinct from those of erythrocytes or leukocytes. For example, CTCs generally have a low membrane potential and a low impedance. Also, cancer cell membranes generally have higher numbers of negatively-charged sialic acid molecules. Due to the differential between the conductance of CTCs and that of the carrier buffer, and due to the cells' relatively large size, distinct signals were recorded by the conductivity sensor, corresponding to single CTCs.

We then seeded 1 mL of whole blood with 10±1 CTCs, pumped the sample through the prototype HTMSU at 2.0 mm/s to concentrate the CTCs into a volume ~190 nL, released the captured cells with trypsin, and counted them with the conductivity sensor at a volumetric flow rate of 0.05 µL/min. See FIG. 3B, showing the measured conductivity data using a 3-point Savitsky-Golay numerical smoothing filter. At a signal-to-noise threshold of 3:1 (=99.7% confidence level), there were 10 peaks in the conductance trace that we assigned to CTCs (indicated with asterisks). Only positive conductance spikes (relative to background) were scored as CTCs, not negative spikes. The "middle" or "baseline" curve also shown in FIG. 3B corresponds to a control sample of whole blood that lacked MCF-7 cells, but that had also been processed through the HTMSU. The CTC scoring system was verified through bright field microscopy, which confirmed that individual CTCs were correlated with positive signals relative to the background conductance, and that the negative signals appeared to be correlated with non-cellular particulates. The disparity in the magnitudes of the CTC peaks evidently arose from differences in cell morphology and composition, perhaps due at least in part to variations in mitotic phase. With the control blood sample (not spiked with CTCs) no conductance signals exceeded the $3\sigma$ criteria, i.e., we achieved a false positive rate of 0 in this particular test.

Example 21

Further Testing of the Conductivity Sensor for Cell Enumeration

To further verify the recovery and detection efficiency of the system, we conducted further tests in which the number of seeded CTCs varied over a broad, physiologically-relevant range (10-250 CTCs per mL of whole blood). See FIG. 3C. The best-fit line for the measured data had a slope of 0.945 with an intercept near 0 ($r^2$=0.9988), indicating an overall recovery and detection rate of ~95% for the CTCs, with a low false negative rate, and a very low false positive rate.

Examples 22-31

Using the Prototype HTMSU to Isolate and Detect Low Abundance LNCaP Prostate Cancer Cells in Whole Blood Prostate tumor cells over-express prostate specific membrane antigen (PSMA). PSMA can be used as a marker to select low-abundance prostate tumor cells from highly heterogeneous clinical samples, including whole blood. We have developed an HTMSU system employing aptamers to specifically bind PSMA. The surface density of the PSMA-specific aptamers on the PMMA surface was ~$8.4 \times 10^{12}$ molecules/cm$^2$. At a linear velocity of 2.5 mm/s, we recovered ~90% of prostate cancer cells from a whole blood sample. Captured cells were subsequently released intact from the surface using 0.25% (w/v) trypsin. The HTMSU device used in these experiments was generally similar to the prototype device described in Examples 1, 3, 4, & 6-14, and depicted in FIG. 1, except as otherwise stated. Neither pre-processing of the blood, nor staining of the cells was required. Nuclease-stabilized, in vitro-generated RNA aptamers were immobilized onto UV-modified sinusoidal capture channels in the HTMSU using carbodiimide coupling chemistry and a linker to enhance accessibility of the surface-bound aptamer.

Example 22

Reagents

The following reagents were purchased from Sigma-Aldrich (St. Louis, Mo.): reagent grade isopropyl alcohol, 1-ethyl-3-[3-dimethylaminopropyl]carbodiimide hydrochloride (EDC), N-hydroxysuccinimide (NHS), fetal bovine serum (FBS) and 2-(4-morpholino)-ethane sulfonic acid (MES). The nuclease-resistant RNA aptamer, ($NH_2$—$(CH_2)_6$—$(OCH_2CH_2)_6$-(ACCAAGACCUGACUUC-UAACUAAGUCUACGUUCC) (SEQ ID NO. 1), was obtained from Eurogentec (San Diego, Calif.). Random sequence oligonucleotides were obtained from Integrated DNA Technologies (Coralville, Iowa). Monoclonal anti-EpCAM antibody was obtained from R&D Systems Inc. (Minneapolis, Minn.). The LNCaP (prostate cancer cell line), MCF-7 (breast cancer cell line), growth media, HEPES buffer, phosphate buffered saline (PBS) and trypsin were all purchased from American Type Culture Collection (Manassas, Va.). Citrated rabbit blood was purchased from Colorado Serum Company (Denver, Colo.). Tris-Glycine buffer was obtained from Bio Rad Laboratories (Hercules, Calif.). All solutions were prepared in nuclease-free water, purchased from Invitrogen Corporation (Carlsbad, Calif.). Nuclease-free microfuge tubes purchased from Ambion Inc. (Foster City, Calif.) were used for the preparation and storage of all samples and reagents. A fluorescein derivative, PKH67, which contains a lipophilic membrane linker for cell staining, was purchased from Sigma-Aldrich (St. Louis, Mo.).

Example 23

Cell Suspensions

LNCaP and MCF-7 cells were cultured to 80% confluence in Dulbecco's Modified Eagle's Medium, supplemented with high glucose, and containing 1.5 g/L sodium bicarbonate ($NaHCO_3$), 15 mM HEPES buffer, and 10% FBS. A 0.25% trypsin solution in 150 mM PBS was used to harvest the LNCaP and MCF-7 cells from the culture plate. LNCaP and MCF-7 cells were stained with PKH67 for fluorescence microscopy, at twice the manufacturer's recommended concentration of PKH67 to more evenly distribute fluorescent labels over the cell surface. Cell counts for seeding experiments in whole blood were determined by counting three aliquots of cells using a hemocytometer. The cell count accuracy was ±10%.

Example 24

Irradiating Channel Surfaces and Forming the HTMSU

The cleaned PMMA devices and cover plates were exposed to ultraviolet (UV) radiation through a mask to form carboxylate moieties on the surface of the capture bed region of the device (but not in other parts of the HTMSU). UV irradiation was transmitted through an aluminum mask for 10 min at 15 mW cm$^{-2}$. The parts were then aligned and clamped together between two borosilicate plates. The cover plate was thermally fused to the substrate in a convective oven. The temperature was increased from 50° C. to 101° C. at a rate of 20° C./min, and held for 15 min. at 101° C., a temperature that is slightly above the glass transition temperature of the UV-modified material. Polyimide-coated, fused silica capillaries were then inserted into the inlet port of the HTMSU to introduce samples into the device with a programmable syringe pump (Harvard, Holliston, Mass.).

Example 25

Conductivity Sensor

Pt electrodes (d=76 µm) were placed in guide channels orthogonal to the fluidic output channel. Insertion of the electrodes was monitored with a microscope to carefully control the inter-electrode gap (50 µm). The cell constant of the conductivity sensor, K, was ~0.01 µm$^{-1}$, chosen to optimize the specific detection of LNCaP cells with an average diameter ~25 µm with electrodes have a diameter ~75 µm.

Example 26

Antibody Immobilization

Antibodies were immobilized in a two step process. The UV-modified thermally assembled HTMSU device was loaded with a solution containing 4 mg/mL EDC, 6 mg/mL NHS, and 150 mM MES (pH=6) for 1 h at room temperature to obtain a succinimidyl ester intermediate. The EDC/NHS solution was then removed by flushing nuclease-free water through the device. Then an aliquot of 1.0 mg/mL of monoclonal anti-EpCAM antibody solution in 150 mM PBS (pH=7.4) was introduced into the HTMSU, and allowed to react for 4 h. The device was then rinsed with a solution of PBS (pH=7.4) to remove any non-specifically bound antibody molecules.

Example 27

Aptamer Immobilization

In one embodiment we employed aptamers as the capture element rather than antibodies. Among the advantages of aptamers are the ordered nature of their attachment to the solid surface (e.g., via the 5' end), rather than the more random locus of attachment with antibodies (e.g., via primary amine groups on the antibody); the ability to carefully control the aptamer/surface distance to improve accessibility; and the robust nature of the molecular recognition elements. Compared to antibodies, aptamers are more easily stored for longer times while maintaining activity. For example, unlike antibodies aptamers may be stored at room temperature without substantial loss of activity.

Figure 5:
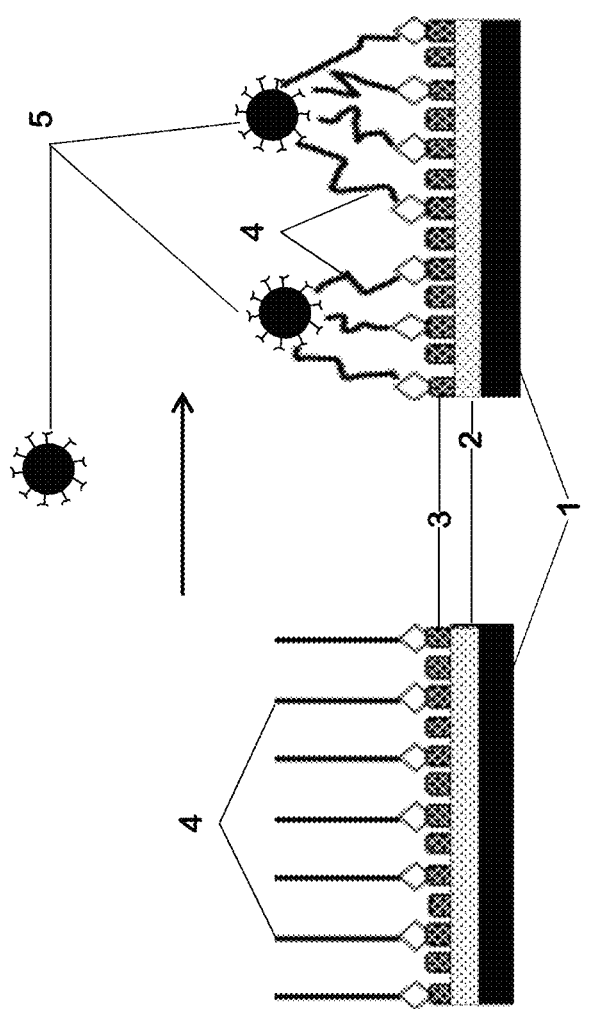
FIG. 5 depicts schematically the immobilization of cells on the surface of a channel in accordance with one embodiment of the invention.

FIG. 5 depicts this embodiment schematically. PMMA film 1, on the interior of the channel, has UV-activated surface layer 2. Activated surface layer 2 is attached via covalent linkages 3 to aptamers 4. LNCaP cells 5 are pumped over the surface, where some of the cells 5 are immobilized by binding to aptamers 4.

Aptamers were immobilized on PMMA surfaces in a single step. Following UV activation, the activated PMMA surfaces were incubated with a solution containing 10 µM either of the PSMA aptamer or of random oligonucleotides, and allowed to incubate for 2-3 h at room temperature. Each oligonucleotide solution also contained 4 mg/mL EDC, and 6 mg/mL NHS in 150 mM MES (pH=6). For decorating planar PMMA films, the PMMA surface was immersed in the reaction solution. Following reaction, the PMMA surface was rinsed with a solution of PBS (pH=7.4) to remove any non-specifically bound constituents.

Example 28

Determination of Aptamer Surface Density

A clean surface plasmon resonance (SPR) gold sensor surface was coated with 300 mL of a PMMA solution (1.0 mg of PMMA in 10 mL of $CH_2Cl_2$) in a custom built spin coater, and was spun at 1,500 rpm for 1 min. The PMMA film was then UV-activated and aptamers were immobilized on the PMMA under conditions otherwise identical to those described above. The SPR response was measured after each treatment with a BIACORE X SPR instrument (Piscataway, N.J.) using DI water. The difference in SPR response before and after aptamer immobilization was used to estimate the number of molecules/cm$^2$ using the manufacturer's published conversion factors.

Example 29

LNCaP Cell Capture

A luer lock syringe (Hamilton, Reno, Nev.) with a luer-to-capillary adapter (Inovaquartz, Phoenix, Ariz.) connected the pump to a capillary, which was in turn sealed to the input port of the HTMSU. A pre-capture rinse was conducted with 0.2 mL of 150 mM PBS at 50 mm/s linear velocity to maintain isotonic conditions. Then the cell suspension was pumped through the HTMSU at a selected velocity, followed by a post-capture rinse with 0.2 mL of 150 mM PBS at 50 mm/s to remove any non-specifically adsorbed cells. The test sample was 1.0 mL of whole blood seeded with 20±1 LNCaP cells, and the control sample was an otherwise identical sample of whole blood without LNCaP cells. The optimal linear flow velocity of 2.5 mm/s was used.

In some instances the HTMSU was fixed onto a programmable motorized stage of an Axiovert 200M microscope (Carl Zeiss, Thornwood, N.Y.). Video images were collected at 30 frames per second (fps) using a monochrome CCD (JAI CV252, San Jose, Calif.). A Xe arc lamp was used to excite the fluorescent dyes incorporated into the cell membranes.

Example 30

Release of Bound LNCaP Cells from the HTMSU

Following the post-cell-capture rinse with PBS, a 0.25% (w/v) trypsin solution in Tris-Glycine buffer (pH=7.4) was pumped through the HTMSU. The captured cells could be observed microscopically until they were released.

Example 31

Counting the Released Cells by Conductivity Measurements

Figure 4A:
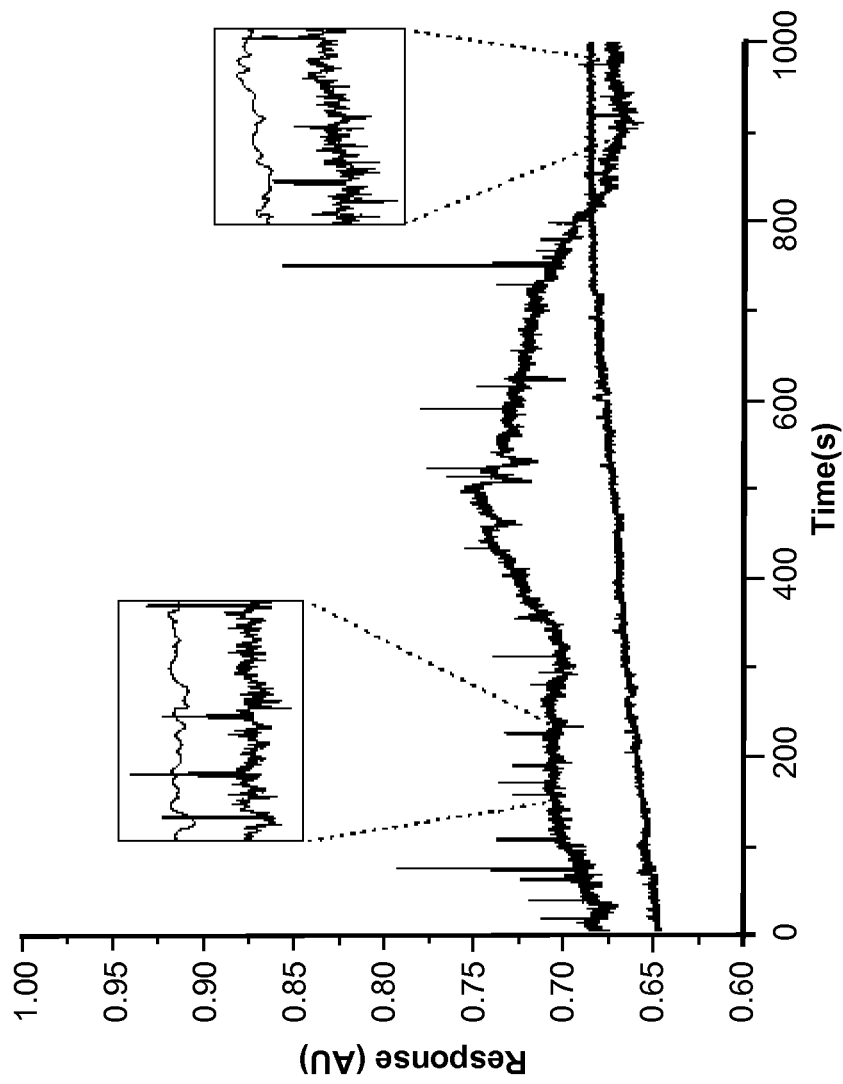
FIGS. 4A & B depict the results of various conductance measurements with the novel system, using LNCaP prostate cancer cells and whole blood.

Released cells were pumped at 0.05 µL/min through the Pt electrodes for counting. Tris-glycine buffer was selected as the major component in the release buffer due to its low conductance; i.e., it is preferred that the buffer should have a conductivity substantially different from that of the target cells, and in general that the buffer's conductivity should be lower than that of the target cells. The conductance response depicted in FIG. 4A exhibited 18 peaks that we assigned to single LNCaP cells, based on a signal-to-noise threshold of 3 (99.7% confidence level). The asterisks designate peaks that were identified as LNCaP cells. The arrowheads represent non-LNCaP cell events. Again, only positive signals were assigned to the target cells; negative spikes, with lower conductance, are believed to have resulted from particulates. The 18 peaks represented a recovery of ~90% of the cells. The insets to FIG. 4A depict magnified views to illustrate the 3:1 signal-to-noise discrimination threshold. The data were smoothed by the Savitsky-Golay method (using a 25 point smoothing function).

The lower curve in FIG. 4A depicts the conductivity measurement for the control sample of whole blood without LNCaP cells. No single-cell spikes were seen in the data trace, indicating that the spikes seen for the LNCaP-seeded whole blood were indeed due to the tumor cells, and that the purity of the LNCaP cell selection was close to 100% (i.e., very few false positives).

Figure 4B:
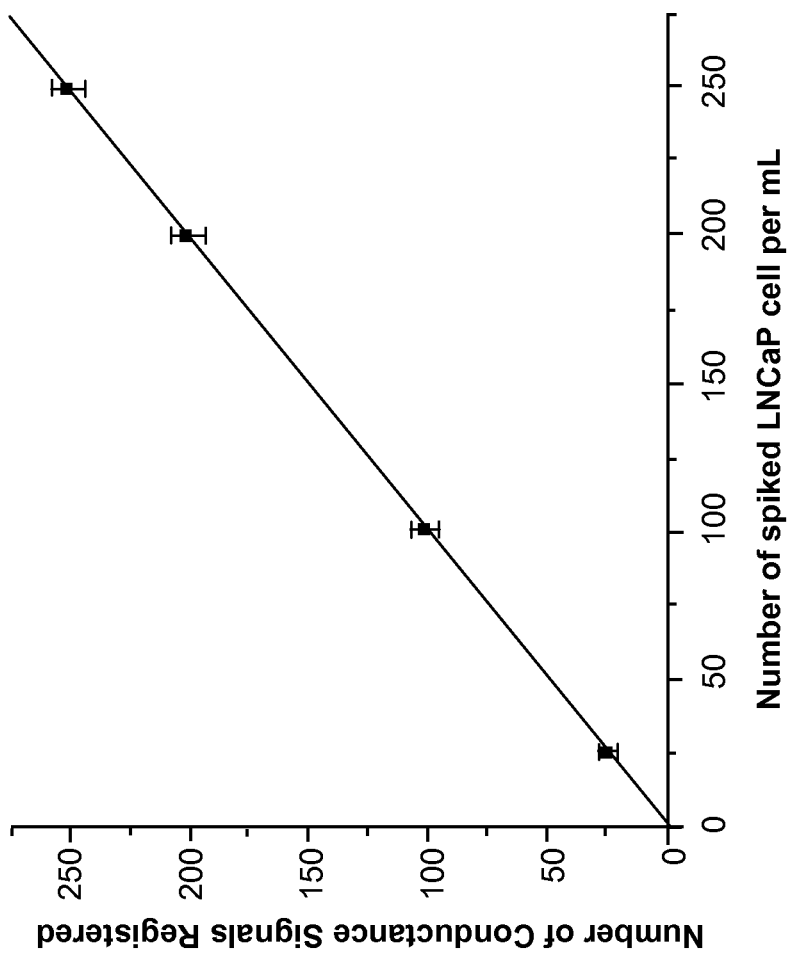

FIG. 4B depicts a calibration plot of "conductivity enumeration" versus the actual number of seeded LNCaP cells, over a range of 10-250 LNCaP cells per mL whole blood. The best-fit linear plot had a slope of 0.990, with an intercept near zero ($r^2$=0.9997). Even at the lowest LNCaP cell load tested, the data still fit the linear function very well. Thus the novel system is well-suited to detect circulating tumor cells in whole blood, even at extremely low concentrations. In 1 mL of whole blood, there are typically about $2.5 \times 10^9$ erythrocytes; thus, at the lowest LNCaP cell load investigated, the enrichment factor was approximately $2.5 \times 10^8$—a difference of eight orders of magnitude. At the optimized flow rate of 2.5 mm/s used in these experiments, the time required to exhaustively process 1 mL of blood was ~29 min.

We observed negligible adhesion of LNCaP cells either to pristine PMMA, or to PMMA linked to random-sequence DNA oligonucleotides. The adhesion forces of the LNCaP cells to these surfaces were not strong enough to withstand the hydrodynamic shear from the laminar fluid flow. However, LNCaP cells were efficiently captured when the PSMA-specific aptamer was tethered to the channel walls.

When the flow velocity is too fast, the resulting decrease in interaction time between cells and the capture elements reduces the number of potential binding events. When the flow is too slow, the reduced velocity leads to a decrease in the encounter rate between the cells and the immobilized recognition element. The optimal flow rate may readily be determined for a given combination of HTMSU configuration, capture element, and target cell type.

We observed maximum cell capture efficiency for LNCaP cells and aptamers at a translational velocity of ~2.5 mm/s, under the conditions employed in this study. By contrast, we found the optimum linear translational velocity for the anti-EpCAM antibody system to be slightly lower, ~2.0 mm/s. It thus appeared that the reaction rate for the EpCAM-antibody interaction was slightly slower than the reaction rate for the PSMA-aptamer interaction.

We also examined the possibility of non-specific adsorption or recognition of other CTC-types using the breast cancer cell line MCF-7 as an example. No MCF-7 cells were seen when the PMMA capture beds were decorated with the anti-PSMA aptamers, and an MCF-7-spiked sample of whole blood was processed as otherwise described above.

There are two principal biosynthetic forms of PSMA in the LNCaP cell membrane: the mannose-rich $PSMA_M$ form, and the glycosylated $PSMA_C$ form. $PSMA_M$ is highly sensitive to trypsin, while $PSMA_C$ is trypsin-resistant. Because trypsin efficiently released the captured LNCaP cells, it appears that the $PSMA_M$ form predominated, or at least that it predominated in attaching to the anti-PSMA aptamers.

Nearly 100% of cells had detached within 7 min after the trypsin had been introduced. Microscopic bright field observation at the Pt electrodes confirmed that the released cells appeared to be intact.

Example 32

Using the Prototype HTMSU to Efficiently Remove Red Blood Cells from Whole Blood Example 32

In another embodiment of the invention, red blood cells ("RBCs" or "erythrocytes") are efficiently removed from a 100 μL sample of whole blood in less than 1 minute using our prototype HTMSU. Aptamers are used to selectively bind the RBCs and clear them from the sample, leaving the white blood cells for further analysis or experimentation. Clearing the RBCs first may make it easier for the larger cells to migrate or diffuse to the channel walls and be captured. Advantages of using the present invention for clearing RBCs as compared to other methods such as centrifugation (i.e., apheresis) is that the clearance can be completed in a very short time period, smaller volumes of blood can be processed, the separation produces purer fractions with a higher recovery of non-cleared cells, and the device can be directly integrated with molecular analysis devices to genotype or otherwise characterize the non-cleared platelet and leukocyte fractions.

In carrying out various molecular analyses and other tests on whole blood, it is often necessary to deplete the sample of RBCs. Centrifugation has been the principal technique previously used to separate fractions of blood, including RBCs, based on their densities. There have been relatively few prior reports of microfluidic techniques for depleting RBCs, and those reports have focused primarily on white blood cell isolation via morphological differences.

An HTMSU as otherwise described in the previous examples is used to rapidly, efficiently, and selectively remove RBCs from samples of whole blood. RBC-specific aptamers are covalently linked to the cell capture bed walls: In one embodiment the aptamer is 5'-CGAATCGCATTGC-CCAACGTTGCCCAAGATTCG-3' (SEQ ID NO. 2), which has been reported to bind specifically to an RBC membrane protein. See K. Morris et al., *Proc. Natl. Acad. Sci. USA*, vol. 95, pp. 2902-2907 (1998). An amino-terminal cross-linker attached to the aptamer (5' $NH_2$—$(CH_2)_6$—$(CH_2CH_2O)_6$— TTTTT-Aptamer) facilitates the formation of a stable amide bond with UV-generated carboxyl groups on the PMMA surface. The $K_D$ for the binding of this aptamer to the RBC membrane protein that it recognizes is ~1.8 nM, and the number of binding sites on the outer membrane of one RBC is ~$6.5 \times 10^3$/cell.

In preliminary tests the HTMSU decorated with RBC-specific aptamers has successfully and efficiently removed essentially all RBCs from a 100 µL sample of whole blood within 1 minute (as determined on conventional hemocytometry slides), while allowing recovery of essentially all WBCs and plasma. In a control HTMSU decorated with random DNA sequences, essentially no RBC clearance was observed.

Using other suitable aptamers (or antibodies), other components may be selectively enhanced or depleted from a sample, for example platelets, neutrophils, other white blood cells, and so forth.

Miscellaneous.

Example 33

Further Uses of the Invention

The invention has been described above largely with respect to embodiments for detecting and enumerating cancer cells in blood. The invention is well-suited for other uses as well. It may be used for detecting and isolating other rare cells in blood or other liquids. For example, it may be used for detecting and isolating fetal cells in maternal blood, or maternal cells in an infant or an adult, or pathogenic bacteria in a water supply, or for isolating stem cells, or other instances of rare cells. The invention may also be used to clear target cells from a sample, e.g., to remove erythrocytes from a test sample, for example prior to screening mRNA from a blood sample; or to remove leukocytes from whole blood, platelets, or plasma prior to transfusion; or to remove tumor cells from bone marrow prior to a bone marrow transplant.

Where applicable, non-specifically bound, potentially interfering cells, e.g., erythrocytes non-specifically adhering to a PMMA surface, can often be dislodged by hydrodynamic shear, simply by increasing the fluid flow rate.

Definitions

As used in the specification and claims, unless context clearly indicates otherwise, the following terms should be understood to have the following meanings:

Two or more channels are "parallel," or fluid flow within two or more channels is "parallel," if the flow occurs (or can occur) in the channels in unison. "Parallel" should be understood as contrasting with "serial" or in "series," a meaning that is analogous to that used in the terminology of electrical circuits. "Parallel" channels may indeed be, but are not necessarily, parallel in the geometrical sense.

"Channels" are separated paths for fluid flow. Multiple channels, even adjacent channels, are physically separated from one another, i.e., they are not in fluidic communication with one another, along most or all of their length. For example, fluid pathways that are separated from one another by walls, such as depicted in FIG. 1, are considered to be "channels" within this definition; even if they may share a common input or a common output, they are physically separated (not in fluidic communication) along most of their length. By contrast, a system in which fluid flow is defined by obstacles such as posts, in which fluid flow along different paths is interleaved and in which fluid paths are in communication with one another, is not considered to constitute "channels" within the scope of this definition, even if there might be certain preferred paths for fluid flow.

Figure 6A:
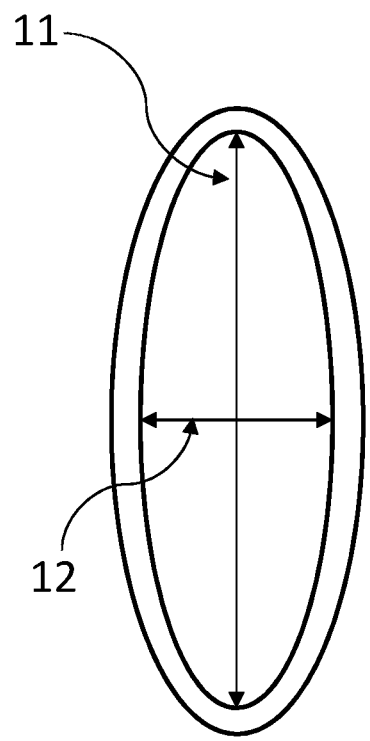
FIGS. 6a and 6b depicts a cross-sectional view of two different exemplary channels in accordance with embodiments of the invention, wherein the height of the channel 11 is at least about three times the width of the channel 12.
Figure 6B:
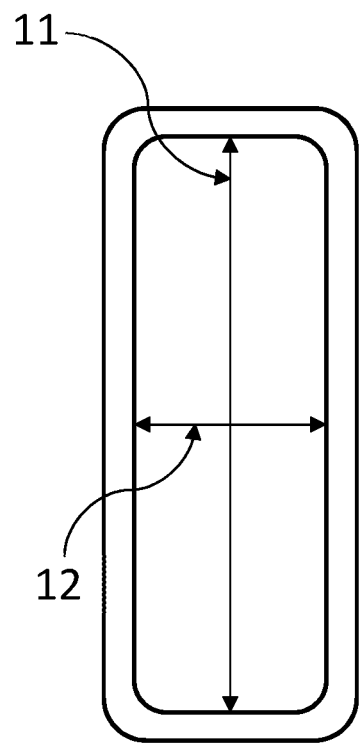

The "length" of a channel is the distance that fluid traverses when going through the channel, along the most direct route from one end to the other. FIGS. 6a and 6b depicts a cross-sectional view of a channel. As shown in FIGS. 6a and 6b, the "width" 12 and "height" 11 of a channel are characteristic dimensions of a cross-section of the channel, both taken in a direction perpendicular to the length of the channel, and also perpendicular to one another. The "width" is generally the smaller of the two characteristic dimensions, and the "height" the larger of the two. The use of the terms "length," "width," and "height" should not be construed to imply that the channel necessarily has any particular shape. The length of a channel will usually be substantially larger than either its width or its height. The "aspect ratio" of a channel is the ratio of its height to its width.

"Sinusoidal" refers to a standard mathematical sinusoid, e.g., one that might be written in the form $$y(x)=A \cdot \sin(kx+\theta)+D$$

"Quasi-sinusoidal" refers to a periodically oscillating channel that may or may not have the shape of a standard sinusoid. As just one possible example, a series of consecutive semicircles, facing in alternating directions and joined to one another end-to-end, would be considered "quasi-sinusoidal." "Sinusoidal" forms are thus a subset of "quasi-sinusoidal" forms.

"Meandering" refers to a channel that fluctuates back and forth relative to the overall direction of fluid flow, but that may or may not have a single, well-defined period, or that may otherwise be irregular. For example, the shape of a river is "meandering." As another example, it may be desirable in some cases to have the period or the amplitude of oscillation in a channel change as a function of position, e.g.:

$$y(x)=A \cdot \sin(kxe^{-mx}+\theta)+D$$

or $$y(x)=A \cdot e^{-mx} \cdot \sin(kx+\theta)+D$$

"Sinusoidal" and "quasi-sinusoidal" channels thus both constitute subsets of "meandering" channels.

In other words, for many purposes it is the alternating change in the direction of fluid flow that is significant, not necessarily the precise mathematical function describing that direction. In practicing the invention, it is preferred that each of the channels should have a sinusoidal, quasi-sinusoidal, or other meandering shape, such that the flow of liquid through a channel tends to cause cells that are suspended in the liquid to contact the capture elements on the channel surface substantially more frequently than would be the case under otherwise identical conditions using an otherwise identical microdevice, but in which the channels were straight.

Note that a "square wave" channel or a "rectangular wave" channel is, by definition, not "sinusoidal." Nor will a "square wave" or "rectangular wave" channel, in general, be considered "quasi-sinusoidal" or "meandering" within the scope of the above definitions. If 90-degree turns are included in a channel path primarily to fold the path of the channel and thereby to increase its length, but the turns are configured in a manner that does not substantially enhance the frequency of contact between suspended cells and the channel surface (even though there might be some small numerical increase), then a "square wave" or "rectangular wave" channel is not considered to be "quasi-sinusoidal" or "meandering." A sinusoidal or quasi-sinusoidal channel imparts a lateral velocity component towards the wall, a lateral velocity that is a function of the curvature. A square wave has a very small radius of curvature at a turn, and zero curvature elsewhere. Thus there are occasional peaks in the lateral component of the velocity, but only of short duration. While the net effect will depend on the particular dimensions and geometry of a particular device, in general the short duration of the peaks in the lateral component for fluid moving through a square wave channel is expected to be substantially less effective in moving cells toward the channel walls than the smaller but longer-acting lateral component in sinusoidal channels.

What are "rare" cells is not susceptible of a precise and quantitative definition; qualitatively, cells are "rare" when their presence is clinically or scientifically significant or potentially significant (e.g., CTCs, pathogenic bacteria), and when their numbers are vastly exceeded by the numbers of other types of cells, or when the rare cells are otherwise present in very low concentrations, such that they are difficult to detect by conventional means. Depending on the context, rare cells might, for example, be those that are present in concentrations less than 100 per milliliter, less than 50 per mL, less than 20 per mL, less than 10 per mL, less than 5 per mL, less than 2 per mL, or less than 1 per mL.

For many purposes, less than ~10 target cells per mL is considered "rare" or "low abundance."

The complete disclosures of all references cited in this specification, including the complete disclosures of the 61/053,727 priority application, are hereby incorporated by reference. Also incorporated by reference are the complete disclosures of A. Adams et al., "Highly efficient circulating tumor cell isolation from whole blood and label-free enumeration using polymer-based microfluidics with an integrated conductivity sensor," *J. Am. Chem. Soc.*, vol. 130, pp. 8633-8641 (2008), and the associated supporting material that is available free of charge from pubs.acs.org; and of U. Dharmasiri et al., "Highly efficient capture and enumeration of low abundance prostate cancer cells using prostate-specific membrane antigen aptamers immobilized to a polymeric microfluidic device," accepted for publication in *Electrophoresis* (2009). In the event of an otherwise irreconcilable conflict, however, the present specification shall control.

What is claimed:

1. A microfluidic device for capturing or isolating circulating tumor cells from a liquid, the microfluidic device comprising:
   a substrate comprising a common fluid input and a common fluid output, a plurality of parallel channels configured to capture or isolate circulating tumor cells and fluidically connected to the common fluid input and the common fluid output, wherein the circulating tumor cells have a mean diameter, and wherein:
   a. a cross-section of each of said plurality of parallel channels has a height and width taken in direction perpendicular to a length of the channels, and the length extends longitudinally from the common fluid input to the common fluid output;
   b. the width of each of said plurality of parallel channels is at least about the mean diameter of the circulating tumor cells, and is not greater than about twice the mean diameter of the circulating tumor cells;

c. the height of each of said plurality of parallel channels is at least about three times the width of each respective channel;
d. at least part of the surface within each of said plurality of parallel channels is covalently linked to one or more capture elements; wherein said capture elements comprise antibodies or aptamers that selectively bind molecules on the membranes of the circulating tumor cells; and
e. each of said plurality of parallel channels has a sinusoidal or quasi-sinusoidal shape.

2. The microfluidic device of claim 1, wherein said capture elements comprise monoclonal antibodies.

* * * * *

SEQUENCE LISTING

```
<160> NUMBER OF SEQ ID NOS: 2

<210> SEQ ID NO 1
<211> LENGTH: 34
<212> TYPE: RNA
<213> ORGANISM: Artificial sequence
<220> FEATURE:
<223> OTHER INFORMATION: PMSA-specific aptamer

<400> SEQUENCE: 1
accaagaccu gacuucuaac uaagucuacg uucc                             34

<210> SEQ ID NO 2
<211> LENGTH: 33
<212> TYPE: DNA
<213> ORGANISM: Artificial sequence
<220> FEATURE:
<223> OTHER INFORMATION: RBC-specific aptamer

<400> SEQUENCE: 2
cgaatcgcat tgcccaacgt tgcccaagat tcg                              33
```